United States Patent
Sastre-Garau et al.

(10) Patent No.: US 7,211,391 B2
(45) Date of Patent: May 1, 2007

(54) METHODS AND COMPOSITIONS FOR PREDICTING THE OUTCOME OF CERVICAL INTRA-EPITHELIAL NEOPLASIA

(75) Inventors: Xavier Sastre-Garau, Vincennes (FR); Isabelle Cartier, Paris (FR)

(73) Assignee: Institut Curie, Paris (FR)

( * ) Notice: Subject to any disclaimer, the term of this patent is extended or adjusted under 35 U.S.C. 154(b) by 0 days.

(21) Appl. No.: 10/987,186

(22) Filed: Nov. 15, 2004

(65) Prior Publication Data

US 2006/0105324 A1    May 18, 2006

(51) Int. Cl.
*C12Q 1/68* (2006.01)
*G01N 33/53* (2006.01)

(52) U.S. Cl. .................. 435/6; 435/7.1; 435/235.1
(58) Field of Classification Search .............. 435/6
See application file for complete search history.

(56) References Cited

U.S. PATENT DOCUMENTS

2004/0202996 A1* 10/2004 Williams et al. ............. 435/5

OTHER PUBLICATIONS

Merriam-Webster Online (p. 1-2).*
Madeleine et al, J of Infectious Diseases, 2002, 186:1565-74.*
Lin et al, Cancer Epidemiology, Biomarkers & Prevention, 2001, 10:1037-1045.*
Trimble et al, Human Cancer Biology, 2005, 11:4717-4723.*
Tockman et al (Cancer Res., 1992, 52:2711s-2718s).*
Slamon et al. (Science vol. 235, Jan. 1987, pp. 177-182).*
Sastre-Garau et al, Obstetrics and Gynecologyl, Oct. 2004, 104:751-755, IDS.*
Villiers et al (Virology, 2004, 324:17-27), IDS.*
Abstract of 19th European Histocompatibility Conference, Genes and Immunity, May 8-11, 2004, Sofia, Bulgaria, vol. 5, Supplement 1.
Villiers et al, Virology 324 (2004) 17-27.

* cited by examiner

*Primary Examiner*—Shanon Foley
*Assistant Examiner*—Laura B Goddard
(74) *Attorney, Agent, or Firm*—Nixon & Vanderhye P.C.

(57) ABSTRACT

The present invention relates to methods and kits for predicting the outcome of cervical intra-epithelial neoplasia and methods for treating a cervical intra-epithelial neoplasia. More particularly, the methods comprise the determination of the presence of the HLA-DRB1*13 allele and the absence of a high risk human papillomavirus (HPV).

8 Claims, 2 Drawing Sheets

Figure 1A:
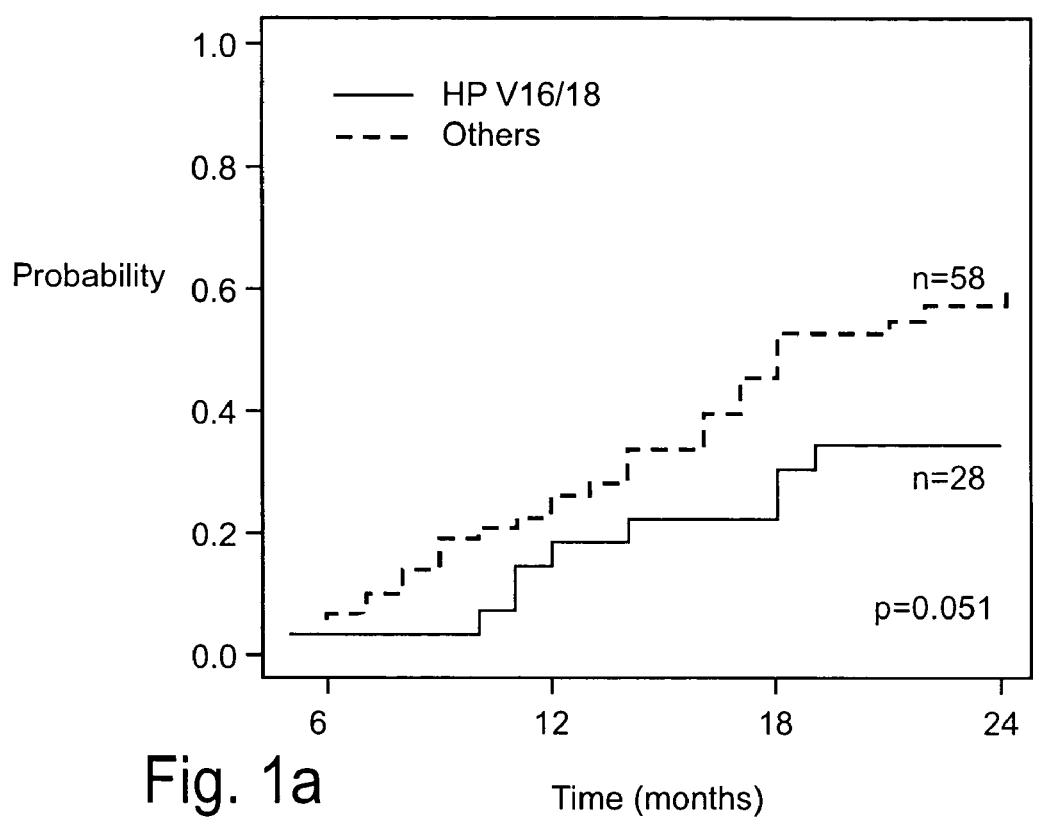

METHODS AND COMPOSITIONS FOR PREDICTING THE OUTCOME OF CERVICAL INTRA-EPITHELIAL NEOPLASIA

FIELD OF THE INVENTION

The present invention relates to methods and compositions for predicting the outcome of cervical intra-epithelial neoplasia.

BACKGROUND OF THE INVENTION

Most neoplasias of the uterine cervix are associated with specific types of human papillomaviruses (HPV). The current concept is that invasive carcinoma are preceded by a long-standing stage of cervical intra-epithelial neoplasia (CIN), an heterogeneous group of disease classified as CIN1, CIN2, or CIN3 according to the severity of their histological abnormalities (Richart R. Obstetrics & Gynecology 1990;75:131–132).

CIN1 are the most frequent lesions, particularly in young women, and may follow different courses without treatment: a spontaneous regression occurs in 50–60% of patients whereas persistence or progression toward CIN2/3 is observed in the remaining cases (Östor A. International Journal of Gynecological Pathology 1993;12:186–192). The oncogenicity of associated-HPV type may influence the disease outcome (Schlecht N F, et al. J Natl Cancer Inst 2003;95(17):1336–43.), but little is known concerning the role of host-linked parameters, such as immunological factors, also likely to be implied in the natural history of these lesions.

Cellular-mediated immunity has been found to be involved in the host response against specific HPV types (Kadish A S, et al. J Natl Cancer Inst 1997;89(17):1285–93.) and may thus account, at least in part, for the regression of CIN. Experimental and clinical studies have also suggested that immunogenetic determinants related to HLA-class II genotype could play a part in tumour progression. In the model of tumours induced in rabbit by the Shope papillomavirus, the regression and malignant conversion of papillomas were found to be linked to the MHC class II genes (Han R, et al. Nature 1992;356:66–68.). In human, positive associations were reported between invasive cervical cancer and DQB1*301 (Madeleine M M, et al. J Infect Dis 2002; 186(11):1565–74.; Wank R, Thomssen C. Nature 1991;352: 723–725.), DQB1*1501 (Apple R J, et al. Nat Genet 1994; 6(2):157–62.) or DQB1*1101 (Madeleine M M, et al. J Infect Dis 2002; Lin P, et al. Cancer Epidemiol Biomarkers Prev 2001;10(10):1037–45.) HLA class II alleles. However, no significant associations were found in other groups of patients (Glew S S, et al. Hum Immunol 1993;37(3):157–64.). In contrast, a negative association of the DRB1*13 allele with cervical cancer developed in patients from different geographic areas has been reported, namely Europe (Apple R J, et al. Journal of the National Cancer Institute 1995;87:427–435.; Sastre-Garau X, et al. Int J Cancer 1996;69(3):159–64.), Africa (Lin P, et al. Cancer Epidemiol Biomarkers Prev 2001;10(10):1037–45.) or North America (Madeleine M M, et al. J Infect Dis 2002;186(11):1565–74.). These data suggest that DRB1*13 alleles may be linked to a protective effect against HPV-associated lesion.

There is a strong need of objective biological criteria which would differentiate CIN corresponding to potential precursors of invasive cancer requiring immediate ablative therapy from those in which the treatment could be withheld for a while. The identification of such a criteria could allow a substantial benefit in terms of cost and morbidity in the care of high grade CIN, especially in young women.

SUMMARY OF THE INVENTION

The present invention discloses objective criteria allowing to predict the outcome of CIN. More particularly, this objective criteria allows to predict the probability of a spontaneous regression of the cervical intra-epithelial neoplasia for a subject. The high probability of a spontaneous regression is linked to the presence of a HLA-DRB1*13 allele. More particularly, a very high probability of a spontaneous regression is linked to the presence of a HLA-DRB1*13 allele and the absence of a high risk human papillomavirus such as HPV16, HPV18 and HPV45.

Therefore, the present invention concerns a method for predicting the spontaneous regression of a cervical intra-epithelial neoplasia in a patient having a CIN comprising:
  obtaining a sample from the patient;
  determining the presence of a HLA-DRB1*13 allele;
  determining the presence of a high risk human papillomavirus (HPV);
  the presence of the HLA-DRB1*13 allele and the absence of a high risk HPV being indicative of a high probability of spontaneous regression of the cervical intra-epithelial neoplasia.

The order of the steps of determining the presence of a HLA-DRB1*13 allele and of determining the presence of a high risk human papillomavirus (HPV) is not important and can be reversed. These steps can be performed consecutively or simultaneously.

In a preferred embodiment, the high risk HPV is selected in the group consisting of HPV16, HPV18 and HPV45. More preferably, the high risk HPV is selected in the group consisting of HPV16, and HPV18.

In a preferred embodiment, the sample is a cervical specimen. Alternatively, the sample is a body fluid sample, preferably a blood sample.

In a first embodiment, said cervical intra-epithelial neoplasia is a low garde cervical intra-epithelial neoplasia. In a second embodiment, said cervical intra-epithelial neoplasia is a high grade cervical intra-epithelial neoplasia.

In a preferred embodiment, said HLA-DRB1*13 allele is HLA-DRB1*1302 allele.

In a preferred embodiment, determining the presence of a high risk human papillomavirus (HPV) in said sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification. In an alternative embodiment, determining the presence of a high risk human papillomavirus (HPV) in said sample is performed by detection of the presence of antibodies against human papillomavirus (HPV) in said sample.

In a preferred embodiment, determining the presence of a HLA-DRB1*13 allele in said sample is performed on nucleic acid by HLA-DRB1*13 allele-specific probe hybridization, by HLA-DRB1*13 allele-specific amplification, by Restriction Fragment Length Polymorphism (RFLP) analysis, or by sequencing, optionally with a previous step of nucleic acid amplification.

By "high probability" is intended that the rate of regression is at least 75%, more preferably at least 90%.

The present invention also concerns a method of treatment of a cervical intra-epithelial neoplasia in a patient having a CIN comprising:
- obtaining a sample from the patient;
- determining the presence of a HLA-DRB1*13 allele;
- determining the presence of a high risk human papillomavirus (HPV); and
- resecting cervical epithelial neoplasm(s) except if the HLA-DRB1*13 allele is present and a high risk HPV is absent.

The order of the steps of determining the presence of a HLA-DRB1*13 allele and of determining the presence of a high risk human papillomavirus (HPV) is not important and can be reversed. These steps can be performed consecutively or simultaneously.

The present invention further concerns a method for selecting patients for resection of cervical epithelial neoplasm(s) in a patient having a CIN, comprising:
- obtaining a sample from the patient;
- determining the presence of a HLA-DRB1*13 allele;
- determining the presence of a high risk human papillomavirus (HPV); and
- selecting patients if the HLA-DRB1*13 allele is absent and a high risk HPV is present.

The order of the steps of determining the presence of a HLA-DRB1*13 allele and of determining the presence of a high risk human papillomavirus (HPV) is not important and can be reversed. These steps can be performed consecutively or simultaneously.

In a preferred embodiment, the high risk HPV is selected in the group consisting of HPV16, HPV18 and HPV45.

In a preferred embodiment, the sample is a cervical specimen.

In a first embodiment, said cervical intra-epithelial neoplasia is a low garde cervical intra-epithelial neoplasia. In a second embodiment, said cervical intra-epithelial neoplasia is a high grade cervical intra-epithelial neoplasia.

In a preferred embodiment, said HLA-DRB1*13 allele is HLA-DRB1*1302 allele.

In a preferred embodiment, determining the presence of a high risk human papillomavirus (HPV) in said sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification. In an alternative embodiment, determining the presence of a high risk human papillomavirus (HPV) in said sample is performed by detection of the presence of antibodies against human papillomavirus (HPV) in said sample.

In a preferred embodiment, determining the presence of a HLA-DRB1*13 allele in said sample is performed on nucleic acid by HLA-DRB1*13 allele-specific probe hybridization, by HLA-DRB1*13 allele-specific amplification, by Restriction Fragment Length Polymorphism (RFLP) analysis, or by sequencing, optionally with a previous step of nucleic acid amplification.

The present invention further concerns a method of treatment of a cervical intra-epithelial neoplasia in a patient having a CIN comprising:
- obtaining a sample from the patient;
- determining the presence of a HLA-DRB1*13 allele;
- determining the presence of a high risk human papillomavirus (HPV);
- following up the cervical intra-epithelial neoplasia evolution if the HLA-DRB1*13 allele is present and a high risk HPV is absent; and
- resecting cervical epithelial neoplasm(s) if the cervical intra-epithelial neoplasia increases.

The order of the steps of determining the presence of a HLA-DRB1*13 allele and of determining the presence of a high risk human papillomavirus (HPV) is not important and can be reversed. These steps can be performed consecutively or simultaneously.

The method can further comprise in addition to the follow up the administration of a treatment for making the cervical intra-epithelial neoplasia stationnary or for curing the cervical intra-epithelial neoplasia.

In a preferred embodiment, determining the presence of a high risk human papillomavirus (HPV) in said sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification. In an alternative embodiment, determining the presence of a high risk human papillomavirus (HPV) in said sample is performed by detection of the presence of antibodies against human papillomavirus (HPV) in said sample.

In a preferred embodiment, determining the presence of a HLA-DRB1*13 allele in said sample is performed on nucleic acid by HLA-DRB1*13 allele-specific probe hybridization, by HLA-DRB1*13 allele-specific amplification, by Restriction Fragment Length Polymorphism (RFLP) analysis, or by sequencing, optionally with a previous step of nucleic acid amplification.

In a preferred embodiment of the methods according to the present invention, the high risk HPV is selected in the group consisting of HPV16, HPV18 and HPV45. More preferably, the high risk HPV is selected in the group consisting of HPV16, and HPV18.

In a preferred embodiment of the methods according to the present invention, the sample is a cervical specimen. Alternatively, the sample is a body fluid sample, preferably a blood sample.

In a first embodiment of the methods according to the present invention, said cervical intra-epithelial neoplasia is a low garde cervical intra-epithelial neoplasia. In a second embodiment, said cervical intra-epithelial neoplasia is a high grade cervical intra-epithelial neoplasia.

In a preferred embodiment of the methods according to the present invention, said HLA-DRB1*13 allele is HLA-DRB1*1302 allele.

In a preferred embodiment, determining the presence of a high risk human papillomavirus (HPV) in said sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification. In an alternative embodiment, determining the presence of a high risk human papillomavirus (HPV) in said sample is performed by detection of the presence of antibodies against human papillomavirus (HPV) in said sample.

In a preferred embodiment, determining the presence of a HLA-DRB1*13 allele in said sample is performed on nucleic acid by HLA-DRB1*13 allele-specific probe hybridization, by HLA-DRB1*13 allele-specific amplification, by Restriction Fragment Length Polymorphism (RFLP) analysis, or by sequencing, optionally with a previous step of nucleic acid amplification.

The present invention concerns a kit for determining the presence of a HLA-DRB1*13 allele and the presence of a high risk human papillomavirus (HPV). Preferably, the high risk HPV is selected in the group consisting of HPV16, HPV18 and HPV45, more preferably from the group consisting of HPV16, and HPV18. In a particular embodiment, the kit comprises:
- a HLA-DRB1*13 allele-specific nucleic acid probe or a HLA-DRB1*13 allele-specific primer pair and, optionally a primer pair for amplifying a HLA-DRB sequence, and
- a nucleic acid probe type-specific of high risk HPV or a primer pair type-specific of high risk HPV, and optionally a primer pair for amplifying a HPV sequence.

LEGEND TO THE FIGURES

FIG. 1a: Probability of regression according to HPV status.

Figure 1B:
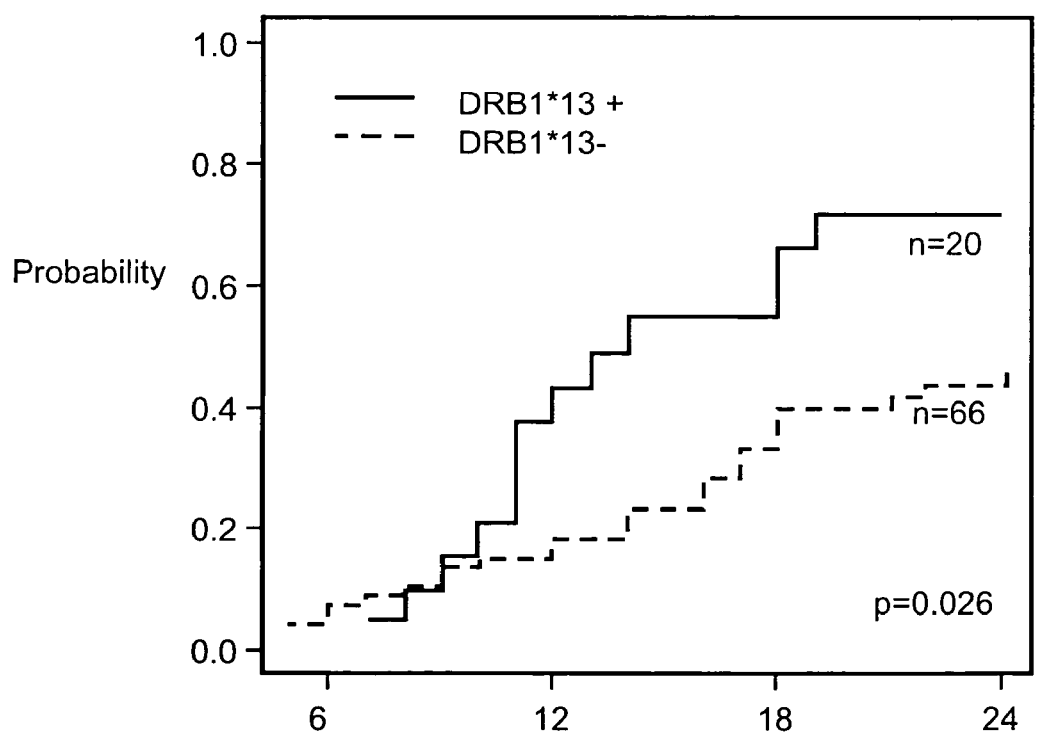

FIG. 1b: Probability of regression according to HLA-DRB1*13.

Figure 1C:
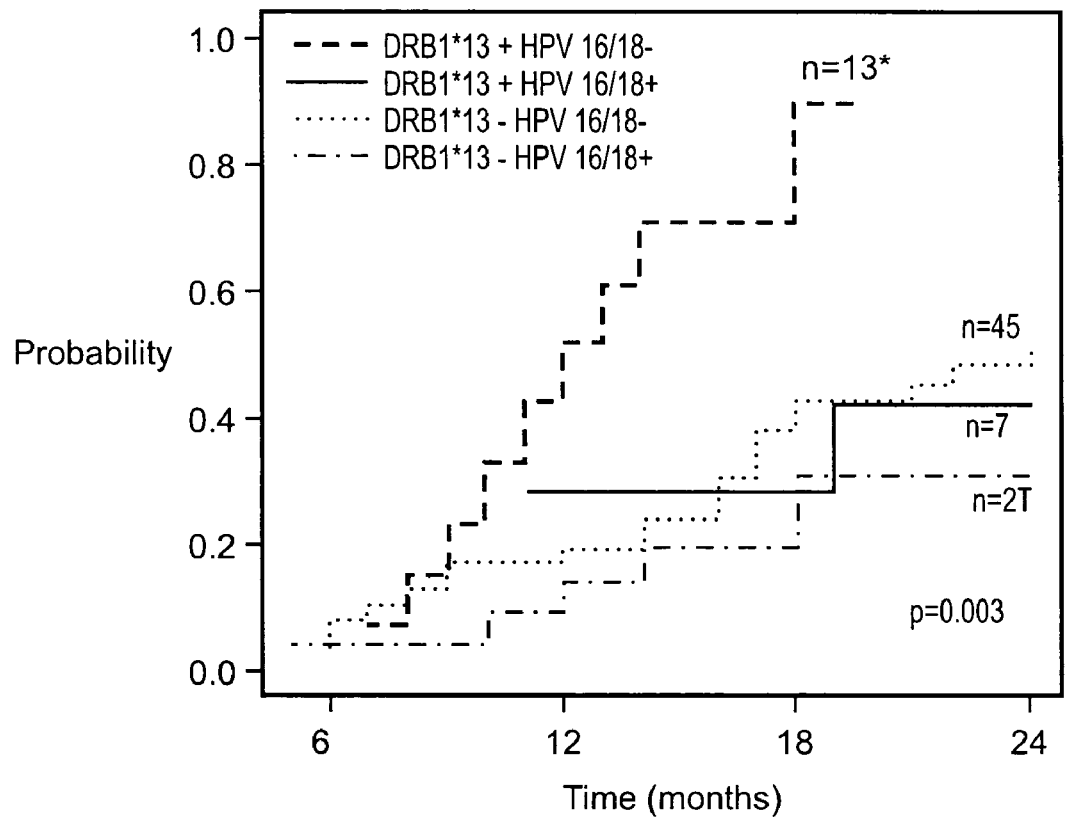

FIG. 1c: Probability of regression according to HLA-DRB1*13 and HPV status.

DETAILED DESCRIPTION OF THE INVENTION

For the first time, the inventors showed that HLA-DR genotypes constitute host factors likely to influence the course of human papillomavirus (HPV)-induced intraepithelial neoplasia of the uterine cervix (CIN). Indeed, the inventors have carried out a prospective study based on the colposcopical follow-up of women with CIN1 and they compared the probability of regression of the lesions according to their HPV and HLA-DR status. They showed that most CIN1, preferably with non HPV16/18, in HLA-DRB1*13 patients experience spontaneous short term regression. This result could serve as a basis to select CIN 2/3 developed de novo to be treated without delay. By "non HPV16/18" is intended that the HPV is an other serotype than HPV16 and HPV18.

Therefore, the outcome of a cervical intra-epithelial neoplasia in a patient, and more particularly its spontaneous regression, can be foreseen by determining the presence of a HLA-DRB1*13 allele and the absence of a high risk human papillomavirus (HPV). The method for predicting the outcome of a cervical intra-epithelial neoplasia can be used in methods of treatment. Indeed, if the cervical intra-epithelial neoplasia has a high probability of regression, the resection of the lesion, which generally is performed when a high grade cervical intra-epithelial neoplasia is detected, can be postponed. Then, the patient will have a follow-up of the neoplasia. The resection will be performed only if a growth or a persistence of the neoplasia is observed. Furthermore, the treatment for preventing or controlling the growth of and/or reducing the risk of developing cervical epithelial neoplasia can be administered to the patient.

An other advantage of the present invention is that the determination of the presence of a HLA-DRB1*13 allele and the absence of a high risk human papillomavirus (HPV) could allow to avoid a colpolscopy, which is an expensive examination.

Therefore, the present invention concerns a method for selecting patients for a colposcopy in a patient having a CIN, comprising:
- obtaining a sample from the patient;
- determining the presence of a HLA-DRB1*13 allele;
- determining the presence of a high risk human papillomavirus (HPV); and
- selecting patients if the HLA-DRB1*13 allele is absent and a high risk HPV is present.

In a preferred embodiment of the present invention, the patient is a human, and more particularly a woman. In a preferred embodiment, the smear test of the patient shows a CIN. More particularly, the patient have a cervical intra-epithelial neoplasia.

The sample can be a body fluid such as blood, serum, plasma, fecal matter, urine, vaginal secretion, spinal fluid, saliva, ascitic fluid, peritoneal fluid, sputum, and breast exudate.

Preferably, the sample is a cervical specimen or biopsy. Said sample comprises cervical cells. More preferably, the sample is a Papanicolaou smear. Methods of obtaining and preparing such samples for use in the method of the invention are known to those skilled in the art ("Theory and Practice of Histological Staining"-Edition Churchill Livingstone-John D Bancroft 4$^{th}$ edition (1996, pp 523–524). The methods according to the present invention are preferably performed on a fraction of the sample consisting predominantly of epithelial cells.

The cervical samples are collected using either a wooden spatula, a Jordan's spatula or various types of cytobrushes. In a preferred embodiment, the cervical specimen is placed immediately into universal bottles containing sterile cold phosphate-buffered saline or the like. In an other embodiment, the sample is collected from a swab test. (<<Cytopathologie gynécologique en milieu liquide>> Edition Elsevier-B. Cochand-Priollet et M. Fabre (2003) pp 16–27)

When the HLA or HPV typing is performed on nucleic acids, the nucleic acids of the sample can be recovered if necessary. These nucleic acids can be DNA or RNA, preferably DNA. The method for recovering nucleic acids from a sample are well known by the man skilled in the art (Maniatis et al, Molecular Cloning, Cold Spring Harbor Laboratory, New York 1982).

The methods according the present inventions comprise a step of determining the presence of a high risk papillomavirus (HSV). The high risk papillomavirus are preferably selected in the group consisting of HPV16, HPV18 and HPV45, more preferably in the group consisting of HPV16 and HPV18. The determination of the presence of a high risk papillomavirus can be performed by any one of the assays known by the man skilled in the art. Such assays can use for HPV typing: hybridization with HPV type specific probe, HPV type specific amplification, Restriction Fragment Length Polymorphism (RFLP), and sequencing. These assays can comprise a previous step of amplification, e.g. by PCR or reverse PCR. The HPV type specific probe can be RNA or DNA probes. In a particular method of typing a human papillomavirus in a patient, HPV DNA sequences are amplified by polymerase chain reaction (PCR) and HPV typing is performed with type-specific nucleic acid probes. For example, see U.S. Pat. No. 5,783,412; U.S. Pat. No. 5,705,627 (incorporated herein by reference). A method of typing a human papillomavirus in a patient can comprise amplifying HPV DNA sequences by PCR using consensus primers which amplify both oncogenic and non-oncogenic HPV types, and then typing HPV by using type-specific DNA probes which hybridize with the amplified region of DNA. This method is further described in U.S. Pat. No. 5,447,839 (incorporated herein by reference). For instance, an other method of typing a human papillomavirus in a patient can comprise: obtaining a sample containing DNA from the human papillomavirus to be typed; amplifying the L1 portion of the human papillomavirus DNA; treating the resulting amplified DNA with a plurality of predetermined restriction enzymes so as to produce restriction fragments; and analyzing the fragments so produces so as to type the human papillomavirus. This method is described in detail in U.S. Pat. No. 5,814,448 (incorporated herein by reference). US 20030143529 (incorporated herein by reference) describes the HPV typing with PNA (peptide-nucleic acid) probes. U.S. Pat. No. 6,482,588 (incorporated herein by reference) describes the HPV typing by PCR and type-specific reverse hybridization. In a further method, the HPV typing is performed by a HPV type-specific amplifcation. For example, a primer specific for HPV16, HPV18 and/or HPV45 is used for performing the PCR amplification of the sample DNA. The primers are designed from nonconserved regions among genital HPV genomes, i.e., located in E1, E4, and E6 open reading frames. The amplified products are analyzed gel electrophoresis and ethidium bromide staining. The method is detailed in Vincent-Salomon et al (1996, Modern Pathology, 9, 614–620) (incorporated herein by reference). In an alternative method, the HPV typing is performed by detection of the presence of antibodies against human papillomavirus (HPV) in body fluids (see U.S. Pat. No. 5,629,146; 5,486,453; U.S. Pat. No. 4,748,109; US 20040110925; incorporated herein by reference).

The following articles, incorporated by reference, also describe method for HPV typing: Ambretti et al, Anal Biochem, 2004, 332, 349–57; Sotlar et al, 2004, J Clin Microbiol, 42, 3176–84; Delrio-Lafreniere et al, Diagn Microbiol Infect Dis, 2004, 48, 23–31; Li et al, J Clin Microbiol, 2003, 41, 5563–71; Venturoli et al, J Virol Methods, 2002, 105, 49–56; Gharizadeh et al, Lab Invest, 2001, 81, 673–9; Vernon et al, J Clin Microbiol, 2000, 38, 651–5; Merkelbach-Bruse et al, Diagn Mol Pathol, 1999, 8, 32–8.

Some kits are commercially available such as Hybrid Capture® 2 HPV DNA Test (Digene, Gaithersburg, Md.), PathoGene® and BioPap® HPV Tests (Enzo Diagnostics, Farmingdale, N.Y.), Amplicor HPV test (Roche, Switzerland), BOIAP REMBRANDT® (Zymed Laboratories, San Francisco, Calif.), Linear Array® HPV Test (Roche, Switzerland) etc . . . .

Briefly, Hybrid Capture® 2 HPV DNA Test comprises the step of releasing nucleic acids from the sample, hybridizing the target DNA with a RNA probe, binding of the DNA-RNA hybrids on a solid support (e.g., through antibodies specific of DNA-RNA hybrids), detecting solid support bound DNA-RNA hybrids with labelled antibodies specific of DNA-RNA hybrids. Hybrid Capture® 2 HPV DNA Test comprises two set of RNA probes: one set for high and medium risk HPV (namely, HPV16, HPV18, HPV31, HPV33, HPV35, HPV39, HPV45, HPV51, HPV52, HPV56, HPV58, HPV59, and HPV68); and one set for low risk HPV (HPV6, HPV11, HPV42, HPV43, and HPV44). See Sargent et al (2004, "A comparison of the Digene Hybrid Capture assay and the Roche A Amplicor Human Papillomavirus (HPV) test for the detection of "High Risk" HPV genotypes in DNA extracts from liquid-based cytology samples collected from women whose cytology was graded "borderline"", "XXIth international papillomavirus conference")

PathoGene® HPV Test is designed for use in determining the type of HPV DNA in infected tissue biopsy sections. Formalin-fixed, paraffin-embedded tissue sections are fixed to pretreated slides, deparaffinized, treated with Proteinase K and then dehydrated. Following these pretreatment procedures, the biopsy sections are stained for the in situ detection and identification of HPV DNA. The In Situ typing assay employs separate mixtures of HPV-specific probes to identify HPV types 6/11, 16/18, 31/33/51. BioPap® HPV Test is is designed for use in determining the type of HPV DNA in cervical smear.

Amplicor HPV test is a PCR-based reagent for the detection of HPV. This test identifies 37 HPV genotypes among which all 13 high-risk genotypes of HPV. See Sargent et al (2004, "A comparison of the Digene Hybrid Capture assay and the Roche A Amplicor Human Papillomavirus (HPV) test for the detection of "High Risk" HPV genotypes in DNA extracts from liquid-based cytology samples collected from women whose cytology was graded "borderline"", "XXIth international papillomavirus conference").

Linear Array® HPV test is a PCR-based reagent for the detection of HPV. See Shepard et al 2004, "The Roche Linear Array HPV test: improved performance over previous research prototypes" "XXIth international papillomavirus conference").

In a preferred embodiment of the present invention, the step of determining the presence of a high-risk HPV is performed with Hybrid Capture® 2 HPV DNA Test (which is approved by FDA).

The methods according the present inventions comprise a step of determining the presence of a HLA-DRB1*13 allele.

In the present invention, the "HLA-DRB1*13 allele" refers to a beta-chain of the HLA class II antigen belonging to the group of alleles which encode DR13 antigen. This group of alleles comprises for example the following alleles: DRB1*130101; DRB1*130102; DRB1*130103; DRB1*130201; DRB1*130202; DRB1*130301; DRB1*130302; DRB1*1304; DRB1*1305; DRB1*1306; DRB1*130701; DRB1*130702; DRB1*1308; DRB1*1309; DRB1*1310; DRB1*1311; DRB1*1312; DRB1*1313; DRB1*131401; DRB1*131402; DRB1*1315; DRB1*1316; DRB1*1317; DRB1*1318; DRB1*1319; DRB1*1320; DRB1*1321; DRB1*1322; DRB1*1323; DRB1*1324; DRB1*1325; DRB1*1326; DRB1*1327; DRB1*1328; DRB1*1329; DRB1*1330; DRB1*1331; DRB1*1332; DRB1*1333; DRB1*1334; DRB1*1335; DRB1*1336; DRB1*1337; DRB1*1338; DRB1*1339; DRB1*1340; DRB1*1341; DRB1*1342; DRB1*1343; DRB1*1344; DRB1*1345; DRB1*1346; DRB1*1347; DRB1*1348; DRB1*1349; DRB1*1350; DRB1*1351; DRB1*1352; DRB1*1353; DRB1*1354; DRB1*1355; DRB1*1356; DRB1*1357; DRB1*1358; DRB1*1359; and DRB1*1360.

The HLA-DRB1 can be typing by means known by the skilled in the art. For example, the HLA-DRB1 can be typing by the PCR-SSP (sequence specific primers) or PCR-SBT (sequence based typing) methods. Methods for typing HLA-DRB1 are for instance described in U.S. Pat. No. 5,567,809; U.S. Pat. No. 6,670,124 (incorporated herein by reference).

Generally, the typing methods comprise a first step of amplification by PCR and a post-amplification step to discriminate between the different alleles (e.g. RFLP, SSOP (Sequence Specific Oligonucleotides Probes, reverse dot blot). In the particular SSP method, the DNA typing is performed directly during the PCR process by using allele-specific primers.

Some kits are commercially available such as INNO-LiPA HLA-DRB1 kit (Innogenetics, Belgium), Micro SSP™ Allele Specific HLA Class II (DRB1*13) (One Lambda, Canoga Park, Calif.), FasType™ DRB Low resolution SSP typing kit or DRB1*13 SSP typing kit (Bio Synthesis, Lewisville, Tex.), etc . . . .

In a preferred embodiment, the determining of the presence of HLA-DRB1*13 is performed with INNO-LiPA HLA-DRB1 kit (Innogenetics, Belgium). This kit is useful for the molecular typing of alleles at allele group level (DRB*01-DRB1*16).

The method can further comprise in addition to the follow up the administration of a treatment for making the cervical intra-epithelial neoplasia stationnary or for curing the cervical intra-epithelial neoplasia. For example, immunotherapy with HPV-derived antigenic peptides can be used for treating the cervical intra-epithelial neoplasia Other examples of such treatments are provided in U.S. Pat. No. 6,486,168 (incorporated herein by reference) by administering Immune Response Modifier, in U.S. Pat. No. 6,462,064 (incorporated herein by reference) by administering an adamantyl retinoid related compound, in U.S. Pat. No. 6,399,645 (incorporated herein by reference) by administering indole-3-carbinol and/or diindolylmethane, in U.S. Pat. No. 6,166,079 (incorporated herein by reference) by administering DFMO.

The present invention also concerns a kit for determining the presence of a HLA-DRB1*13 allele and the presence of a high risk human papillomavirus (HPV). Preferably, the kit detects the presence of the high risk HPV selected in the group consisting of HPV16, HPV18 and HPV45, preferably HPV16 and HPV18. More particularly, the kit according to the present invention comprises the appropriate primers and probes for detecting the HLA-DRB1*13 allele, and the HPV16 and HPV18 papillomavirus. The kit according the present invention comprises the essential elements necessary for performing the typing methods described above.

Further aspects and advantages of the present invention will be disclosed in the following experimental section, which should be regarded as illustrative and not limiting the scope of the present application.

EXAMPLES

Objective: HLA-DR genotypes constitute host factors likely to influence the course of human papillomavirus (HPV)-induced intraepithelial neoplasia of the uterine cervix (CIN). In particular, HLA-DRB1*13 allele frequency has been found lower in different series of women with invasive cervical cancer than in the general population, suggesting that this allele could exert a protective effect against the progression of cervical neoplasia. In order to test this hypothesis, the inventors have designed a prospective study of low grade CIN (CIN1) and analysed the probability of regression of these lesions according to the HLA-DR and HPV status in patients.

Methods: The series was composed of 86 women with CIN1 who agreed with colposcopic regular follow-up and no immediate treatment. Biopsy specimens were taken under colposcopy for histology and for the determination of HPV and HLA status. Cases were classified in: regression, persistence for at least 12 months or progression toward CIN2/3.

Results: The overall 24-months rate of spontaneous regression was 51.6%. This rate was 34.7% in cases associated with HPV 16/18 and 59.9% in the remaining cases (p=0.051). Comparison of disease outcome with the HLA status showed that the rate of regression was 71.8% in patients with HLA-DRB1*13 and 45.9% in patients with any other genotypes (p=0.03). Moreover, the rate of regression reached 90.5% at 18 months in DRB1*13 patients with non HPV16/18-associated CIN. In multivariate analysis, HLA-DRB1*13 allele and negative HPV16/18 status were independently associated with an increased probability for regression (HRa=2.5[1.3–5.1] and HRa=2.4[1.1–5.3], respectively).

Conclusion: These results show that it is possible to define the subset of CIN1 likely to experience spontaneous short term regression using two biological parameters characterising the viral etiological agent and the host, respectively. Whether this association could be extended to the course of CIN2/3 would be of major practical interest for the care of these lesions.

Patients and Methods

The cohort analysed was composed of 86 consecutive patients with CIN1, referred for a colposcopy due to an abnormal PAP smear, and who agreed with colposcopic regular follow-up and no immediate treatment. Colposcopies and histological analyses were performed by a single expert gynaeco-pathologist (Dr IC). All colposcopies were carried out under strict estrogen conditions in order to optimise endocervical examination and visualisation of the squamous-columnar junction. Two contiguous biopsy specimens of the lesion were taken under colposcopic control, one fixed in Bouin's solution for histological analysis and the other one frozen for HPV and HLA typing. Only cases with fully seen squamous-columnar junction and CIN1 were included in the study. The follow-up protocol included a second colposcopy with biopsy 10–12 months after the first diagnosis of CIN1, then a consultation with colposcopy every year. Some patients consulted earlier for personal convenience. Cases were classified in 3 categories: regression when no more evidence of CIN was found at colposcopical and histological analyses performed during the follow-up, persistence when the lesion remained a CIN1 over a period of at least 12 months, and progression when the subsequent histology was CIN2 or 3.

HPV typing was performed as previously reported (Sastre-Garau X, et al. Int J Cancer 1996;69(3):159–64.). Cases positive with Polymerase Chain Reaction technique using consensus primers (GP5+/GP6+) only were referred as HPVX. An aliquot of DNA sample, extracted from tumour tissue specimens for HPV typing, was also used for HLA typing. DQA1, DQB1 and DRB1 typing was performed by PCR SSO reverse dot blot (Innolipa, Innogenetics, Ghent, Belgium).

For statistical analysis, chi-square tests, or Fisher' exact tests when appropriate, were used to compare proportions. The inventors estimated the risk of regression at 24 months using the Kaplan Meier product-limit method. Log rank tests were used for comparing the risk of regression between the subgroups of potential risk factors. Cox model was used for multivariate analysis. All tests were two-tailed and differences were considered significant when p<0.05. The analysis was carried out using the Splus statistics package.

Results

Mean age of patients was 31 (18–70). During the follow-up (median length 24 months), 41/86 cases experienced regression whereas the lesion remained CIN1 in 27 cases and progressed toward CIN2/3 in 18 cases (Table 1). HPV DNA sequences were detected in 69 (80%) cases (Table 1). Sequences detected correspond to HPV 16 (26 cases), HPV 33 (7 cases), HPV 31 (5 cases), HPV51 (3 cases), HPV 6, 18, 35, 51 (2 cases each) and HPV X (20 cases). HLA-DRB1*13 genotype was found in 20 (23%) cases (Table 1), among which 9 cases corresponded to DRB1*1301, 9 cases to DRB1*1302, and 2 cases to DRB1*1303. Analysis of the disease outcome showed that the overall rate of regression was 23.8% at 12 months and 51.6% at 24 months. This rate was 61.9% in women under 30 and 36.8% in women over 30

(p=0.03). Comparing the course of the disease to the HPV status, the rate of regression was 34.7% at 24 months in cases associated with HPV 16/18 and 59.9% in the remaining cases (p=0.051) (FIG. 1a). Comparison between HLA-DR status and disease outcome showed that the 24-months rate of regression was 71.8% in patients with HLA-DRB1*13 and 45.9% in patients with any other genotypes (p=0.03) (FIG. 1b). It is worth mentioning that 8/9 patients with DRB1*1302 genotype experienced regression.

TABLE 1

Course of CIN1 according to HPV and HLA-DRB1*13 status

| Course of CIN1 | N of cases | HPV Typing | | | HLA-DRB1*13 |
|---|---|---|---|---|---|
| | | 16/18 | non 16/18 | negative | |
| | 86 | 28 (33%) | 41 (47%) | 17 (20%) | 20 (23%) |
| Regression | 41 | 9 (22%) | 23 (56%) | 9 (22%) | 13 (32%) |
| Persistence | 27 | 9 (33%) | 13 (48%) | 5 (19%) | 4 (14%) |
| Progression | 18 | 10 (56%) | 5 (27%) | 3 (17%) | 3 (17%) |

The probability of regression was also analysed according to HPV and HLA-DRB1*13 status. In the group of HLA-DRB1*13 patients with non HPV 16/18-associated CIN1, the regression rate was 90.5% (FIG. 1c). In contrast, this rate was only 31.8% in patients with non HLA-DRB1*13 allele and presenting CIN1 associated with HPV 16/18, and it was 42.9% and 52.1% in the two other groups (FIG. 1c) (p=0.003). The adjusted hazard ratio for regression within 24 months in HLA-DRB1*13 patients as compared with that in patients with other alleles was 2.5[1.3–5.1] (p<0.01), and that in patients with negative HPV16/18 status as compared with those with HPV16/18 positive status was 2.4[1.1–5.3] (p=0.02). No significant interaction was found between HPV status and DRB1*13 status which behave as independent factors. Furthermore, no significant association was observed between the course of CIN1 and the frequency of other alleles reported to present positive or negative association with invasive cancer such as DRB1*1001, DRB1*1101, DRB1*1501, DRB1*0301, or DQB*0301 . . . (data not shown).

Discussion

The prospective study of the inventors shows that the course of most CIN1 is related to both the associated-HPV type and the HLA-DR genotype of the patients. More than 90% of CIN1 in HLA-DRB1*13 patients with non HPV16/18 status experienced spontaneous short term regression. The HLA-DRB1*13 genotype frequency was 23% in our CIN1 patients, a rate similar to that found in the general population, but significantly higher than that reported in patients from various ethnic groups with invasive carcinoma of the cervix. This difference fits well with the increased rate of regression of CIN1 in HLA-DRB1*13 patients observed in the present study. Such a positive association could be related to any gene(s) linked to DRB1*13. However, the DRB1*1302 genotype was more closely associated with the disease outcome than the DRB1*1301/1303 genotypes and was not found to be preferentially associated with any specific HLA-DQ alleles (data not shown). These facts advocate for a role of the DRB1*1302 gene product in the immune response against HPV infection but the involvement of other gene(s) associated with this allele cannot be excluded. The inventors did not observe any specific HPV type in the HLA-DRB1*13 patients. Further analyses are necessary to specify whether HPV peptides common to various viral types may be presented by the HLA-DRB1*13 and lead to an efficient immune response, accounting thus for the association observed. In HPV16/18-associated lesions, the DRB1*13 positive effect might be balanced by the high oncogenicity of these virus types. It is also to be reminded that, even in the less favourable situation of non HLA-DRB1*13 patients presenting CIN1 associated with HPV16/18, the spontaneous rate of regression was still about 30%. The increased frequency of the DQB1*0301 allele, reported in series of CIN1/2 (Vandenvelde C, et al. The Lancet 1993;341:553.) or CIN3 (David A, et al. The Lancet 1992;340:52.; Odunsi K, et al. Int J Cancer 1996;67 (5):595–602.) was not found in the present population of patients.

In conclusion, the analysis of the inventors showed that the regression of CIN1 was preferentially associated with the HLA-DRB1*13 genotype, particularly in cases with HPV types of intermediate oncogenicity. The outcome of CIN1 could thus be predicted, in a large proportion of cases, by the assessment of viral and host-immunogenetic factors. Most CIN1 do not require specific treatment. However, the classical concept of progression from CIN1 to CIN2/3 is controversial (Wright T C, Kurman R J. Papillomavirus Report 1994;5:175–182.) and it has been shown that high grade CIN may develop de novo. Whether these results could be extended to the course of CIN2/3 is a major matter. In this context, it is to be stressed that the proportion of DRB1*13 patients with non HPV16/18 status represented less than 2% of the population of invasive cancers analysed in a previous study (Sastre-Garau X, et al. Int J Cancer 1996;69(3):159–64.). This, added to the fact that DRB1*13 genotype frequency was found to be decreased in women from various geographic origin with invasive cancer, strongly suggests that the natural history of high grade CIN also depends, at least partly, on the HLA-DR and HPV status of patients. Objective biological criteria would thus differentiate CIN2/3 corresponding to potential precursors of invasive cancer requiring immediate ablative therapy from those in which the treatment could be withheld for a while. This attitude would most likely allow a substantial benefit in terms of cost and morbidity in the care of high grade CIN, especially in young women. Furthermore, the definition of the viral epitopes which are probably at the basis of this association may be of interest in the field of prophylactic or curative immunotherapy.

What is claimed is:

1. A method for determining the probability to have a spontaneous regression of a cervical intra-epithelial neoplasia 1 (CIN1) in a patient having a cervical intra-epithelial neoplasia 1 (CIN1) comprising:
   obtaining a cervical specimen sample from the patient;
   determining the presence of HLA-DRB1*1302 in said sample; and
   determining the presence of a human papillomavirus (HPV) 16 and HPV18 in said sample;
   the presence of the HLA-DRB1*1302 allele and the absence of a high probability of spontaneous regression of said cervical intra-epithelial neoplasia (CIN1).

2. The method according to claim 1, wherein determining the presence of human papillomavirus (HPV) in said cervical specimen sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification.

3. The method according to claim 1, wherein determining the presence of the human papillomavirus (HPV) in said cervical specimen sample is performed by detection of the presence of antibodies against human papillomavirus (HPV).

4. The method according to claim 1, wherein determining the presence of a HLA-DRB1*1302 allele in said sample is performed on nucleic acid by HLA-DRB1*1302 allele-specific probe hybridization, by HLA-DRB1*1302 allele-specific amplification, by Restriction Fragment Length Polymorphism (RFLP) analysis, or by sequencing, optionally with a previous step of nucleic acid amplification.

5. A method for determining the probability to have a spontaneous regression of a cervical intra epithelial neoplasia 1 (CIN 1) in a patient having a cervical intra epithelial neoplasia 1 (CIN1) comprising:
  obtaining a cervical specimen sample from the patient;
  obtaining at least one of a blood, a serum or a plasma sample from the patient; determining the presence of a HLA DRB1*1302 allele in said at least one of a blood, serum or plasma sample; and,
  determining the presence of a human papillomavirus (HPV) HPV16 and HPV18 in said cervical specimen sample;
  the presence of the HLA DRB1*1302 allele and the absence of HPV16 and HPV18 being indicative of a high probability of spontaneous regression of said cervical intra epithelial neoplasia 1 (CIN1).

6. The method according to claim 5, wherein determining the presence of human papillomavirus (HPV) in said cervical specimen sample is performed on nucleic acid by HPV type-specific probe hybridization, by HPV type-specific amplification, by Restriction Fragment Length Polymorphism (RFLP) analysis, or by sequencing, optionally with a previous step of nucleic acid amplification.

7. The method according to claim 5, wherein determining the presence of the human papillomavirus (HPV) in said cervical specimen sample is performed by detection of the presence of antibodies against human papillomavirus (HPV).

8. The method according to claim 5, wherein determining the presence of a HLA-DRB1*1302 allele is performed on nucleic acid by HLA-DRB1*1302 allele-specific probe hybridization, by HLA-DRB1*1302 allele-specific amplification, by Restriction Fragment Length Polymorphism (RFLP) analysis, or by sequencing, optionally with a previous step of nucleic acid amplification.

* * * * *

UNITED STATES PATENT AND TRADEMARK OFFICE
CERTIFICATE OF CORRECTION

| | | |
|---|---|---|
| PATENT NO. | : 7,211,391 B2 | Page 1 of 1 |
| APPLICATION NO. | : 10/987186 | |
| DATED | : May 1, 2007 | |
| INVENTOR(S) | : Sastre-Garau et al. | |

It is certified that error appears in the above-identified patent and that said Letters Patent is hereby corrected as shown below:

Column 12, lines 56-57 (lines 10-11 of claim 1): delete "the presence of the HLA-DRB1*1302 allele and the absence of a high probability of spontaneous regression" and insert therefor --the presence of the HLA-DRB1*1302 allele and the absence of HPV16 and HPV18 being indicative of a high probability of spontaneous regression --.

Signed and Sealed this

Twentieth Day of November, 2007

JON W. DUDAS
*Director of the United States Patent and Trademark Office*